(12) United States Patent
Graether

(10) Patent No.: US 6,675,805 B1
(45) Date of Patent: Jan. 13, 2004

(54) METHOD AND APPARATUS FOR DRAPING AN EYE FOR SURGICAL PROCEDURES

(76) Inventor: John M. Graether, 611 Elmwood Dr., Marshalltown, IA (US) 50158

( * ) Notice: Subject to any disclaimer, the term of this patent is extended or adjusted under 35 U.S.C. 154(b) by 0 days.

(21) Appl. No.: 10/370,544

(22) Filed: Feb. 20, 2003

(51) Int. Cl.[7] ................................................ A61B 19/00
(52) U.S. Cl. ...................................... 128/849; 128/856
(58) Field of Search ................................. 128/849–856; 600/107, 236

(56) References Cited

U.S. PATENT DOCUMENTS

| | | |
|---|---|---|
| 5,213,114 A | 5/1993 | Bailey, Jr. |
| 5,433,190 A | 7/1995 | Sunalp |
| 5,632,284 A | 5/1997 | Graether |
| 6,440,065 B1 | 8/2002 | Hered |

Primary Examiner—Michael A. Brown

(57) ABSTRACT

A method and apparatus for draping an eye for surgical procedures has a drape fabric with a center opening. A resilient U-shaped speculum is attached to the drape fabric at the center opening and is attached to the periphery thereof. The speculum has two spaced upstanding clips that can be compressed together to diminish the area of the speculum, so that it can be inserted into the eye underneath the eyelids. Release of the compressive pressure allows the speculum to expand within the eye against the underneath portion of the eyelids. Then drape material around the speculum is then folded over the speculum and the eyelid margins to expose the globe of the eye but to completely cover the eyelids and the eyelashes.

20 Claims, 11 Drawing Sheets

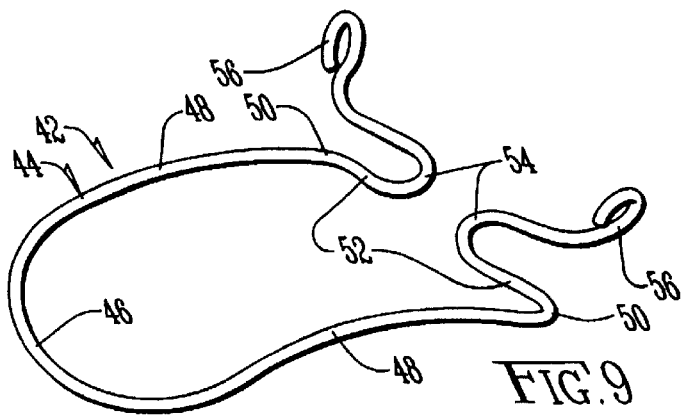
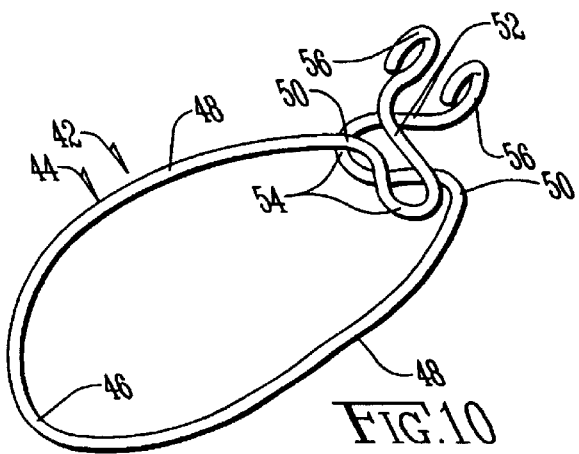
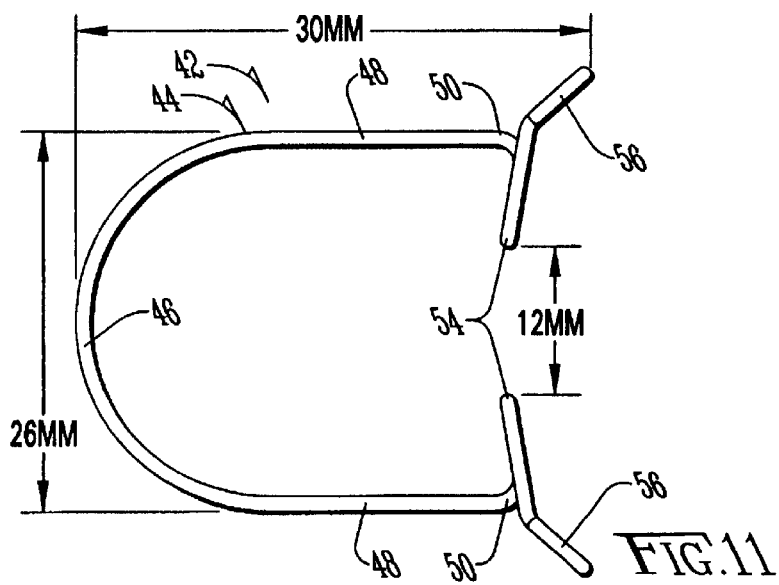

METHOD AND APPARATUS FOR DRAPING AN EYE FOR SURGICAL PROCEDURES

BACKGROUND OF THE INVENTION

It is well known that the majority of intraocular infections related to surgery are caused by organisms from the patient's own lids and lashes. Many different styles of draping the eye for surgery have been advanced, but none has adequately and consistently isolated the surgical field from potential contamination from the surrounding tissues. Also, present methods of draping and the intrusion of an external speculum may limit access to the surgical field or impede a view of the field through the surgical microscope. A separate speculum may cause external pressure on the eye, which can be dangerous, when the eye is open for surgical maneuvers.

It is therefore the objective of this invention to provide a method and apparatus for draping an eye for surgical procedures which will have the following characteristics:

1. It must effectively and consistently isolate the surgical field from the lids and lashes.
2. It must be easy to apply and remove.
3. It must be comfortable under topical anesthesia.
4. It must provide good exposure of the surgical field.
5. It must not cause excessive external pressure on the globe.
6. It must be economical to use in both cost and time.
7. It must allow adequate drainage of debris from the surgical field.

SUMMARY OF THE INVENTION

The speculum-drape of the invention has two components: (1) a thin (50 mm) polyethylene drape fabric and (2) a stainless-steel wire speculum. The two are joined at a central aperture by flaps secured with a water-resistant, double-sided adhesive tape or by ultrasonic welding to anchor the flaps to the surrounding fabric. The speculum is self-retaining, anchored by clips to the lid margin and the internal ring structure. The spring action on the lid margin and the traction on the drape fabric open the lid aperture for surgery. No speculum separate from the drape is usually required.

The external clips and tabs of the U-shaped speculum make it easy to compress the drape for insertion beneath the lids and anchor the speculum to the lids when released. The arcuate closed end of the speculum engages the under surface of the lid especially at the outer canthus tendon and creates a three point stable fixation for the speculum.

The closed end of the speculum also presents a smooth, rounded surface that makes insertion beneath the lid atraumatic. When in place, the aperture in the drape fabric contacts the bulbar conjunctive to form a seal, and the drape completely covers and isolates the lids and lashes from the surgical field. Because the traction on the lids by the fabric is in a direction away from the eye, no external pressure is induced to raise the intraocular pressure or distort the globe.

To anchor it in place after insertion, the speculum-drape has adhesive strips attached to the undersurface with a pull-off membrane to expose the adhesive. Alternatively, the drape may be supplied with a separate double adhesive U-shaped device that would be placed around the eye prior to insertion of the drape.

BRIEF DESCRIPTION OF THE DRAWINGS

FIG. 9 is an enlarged scale perspective view of the speculum of the invention in an expanded position;

FIG. 10 is an enlarged scale perspective view of the speculum of the invention in a compressed position;

FIG. 11 is a plan view of the speculum in the slightly compressed state when it is attached to the drape material;

BRIEF DESCRIPTION OF THE EMBODIMENTS OF THE INVENTION

Figure 1:
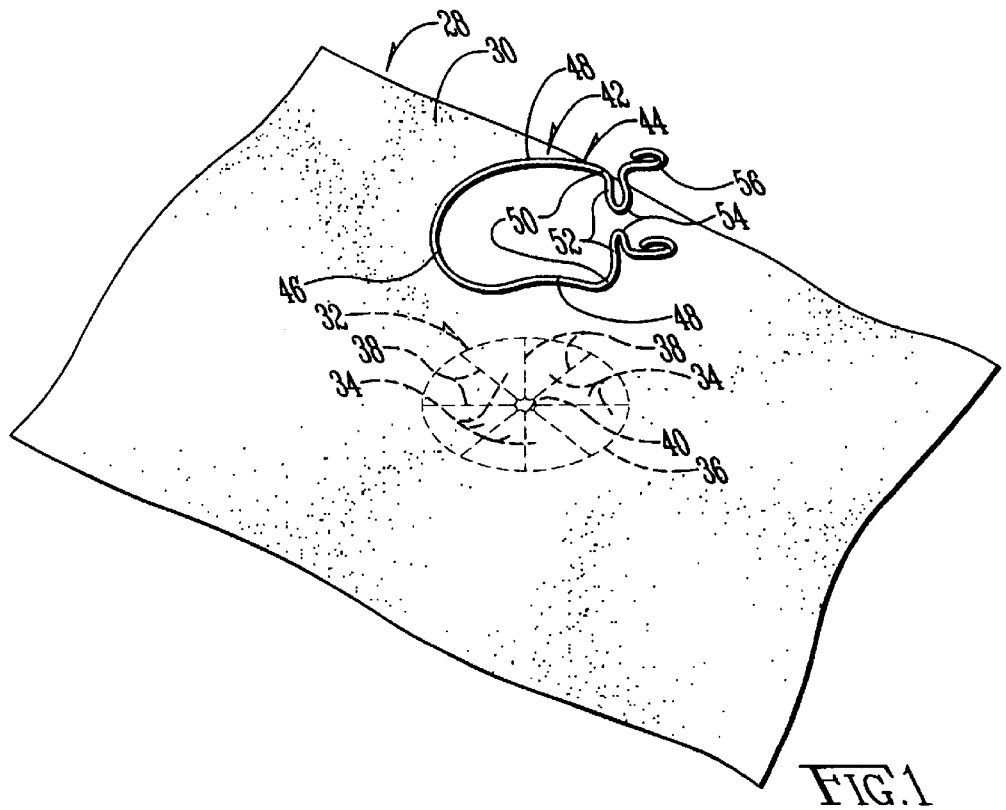
FIG. 1 is a reduced scale exploded perspective view of the drape material and speculum before assembly.

The following terms and meanings will be used in part to describe the invention:

1. Speculum-Drape: An integrated device that serves as both a drape to cover and isolate the lids and lashes as well as a speculum to open the lids to expose the eye for surgical procedures.

2. Speculum: The wire structure that is attached to the drape fabric. It is formed from 0.71-mm stainless steel wire. It is a spring that helps hold the lid open for surgery and carries the drape fabric beneath the lid.

3. Clip: That portion of the speculum wire that engages the external lids at the nasal aspect.

4. Gap: The space or distance between the hooks (clips) for the upper and lower lids. The gap generates the opening between the lids to expose the eyeball.

5. Hoop: The smoothly curved portion of the wire opposite the open end of the speculum. It forms the leading edge of the device that is inserted first beneath the lids and ultimately comes to lie in the temporal fornix of the conjunctival sac. With the drape in place, the curved end of the hoop lies beneath the lids.

6. Arm: The relatively straight side portions of the speculum wire between the hoop and the clip.

7. Shoulder: The junction of the arm and the hook or clip where the speculum wire is bent 10° to start the clip.

8. Three Point Fixation: The principal anchoring points of the speculum are the terminal clips attached to the upper and lower lids and the end of the hoop resting beneath the lateral canthus tendon. The entire speculum wire with attached drape rests against the underside of the upper and lower lids, but the three principal points of support are as noted.

9. Tab: The terminal end of the speculum wire that is turned back to form a loop that is used to compress the speculum wire in order to insert the drape into the conjunctival fornix.

10. Spring Tension: The static energy created by deforming the speculum spring wire.

11. Natural State: The shape of the wire speculum when no pressure is applied.

12. Compressed State: The reduced dimensions produced by pressure on the terminal tabs that reduce the diameter of the hoop for insertion beneath the lids. In maximum compression the hooks overlap but do not lock together and the tabs are brought into close proximity by the pressure of the thumb and finger.

13. Drape Fabric: The 35–50 micron film of low-density polyethylene that forms the fabric portion of the speculum-drape. It is microembossed on the upper surface to form a mat or non-reflective surface and glossy on the lower (under) surface to adhere to the lid skin. A preferred drape material is the fabric used in Steri-Drape 1035 manufactured by the 3M Company of Minneapolis, Minn.

14. Gutter: The gutter refers to a drainage passage created by a crease or fold in the drape to allow fluid to escape by gravity or capillary attraction from the surgical field. With the speculum-drape, traction on the temporal aspect of the drape fabric will cause a fold to form from the attachment of the fabric to the wire hoop beneath the lateral canthus to the point of traction. That point can be fixed by an adhesive patch attaching the drape to the temporal face, or a metal clip attached to the fabric, creating such a channel for drainage.

15. Palpebral Aperture: The opening between the lids that expose the eye.

16. Fornix: The terminal portion of the conjunctival sac, particularly the lateral aspect.

17. Surgical Field: The area of the eye and adnexa directly involved in or adjacent to the surgical operation. This area must be rendered aseptic to avoid the risk of surgical infection. Generally, the surgical field must be isolated from the lids and lashes as these structures often harbor bacteria as normal flora. These bacteria can become pathogenic if introduced into the surgical incision or the interior of the eye. The patient's lids and lashes are the most common origin for bacteria that are the cause of endophthalmitis.

18. Topical Anesthesia: Ophthalmic anesthesia obtained by drops or gel applied directly to the cornea and conjunctiva. It is often supplemented by sedation. In recent years, it has become the most frequent form of anesthesia for cataract and refractive surgery.

19. Endophthalmitis: This is an infection within the eyeball usually caused by bacteria introduced at the time of surgery or in the immediate postoperative period. This infection is most commonly associated with surgical operations that require entry into the interior of the eye such as cataract or glaucoma procedures.

Figure 6:
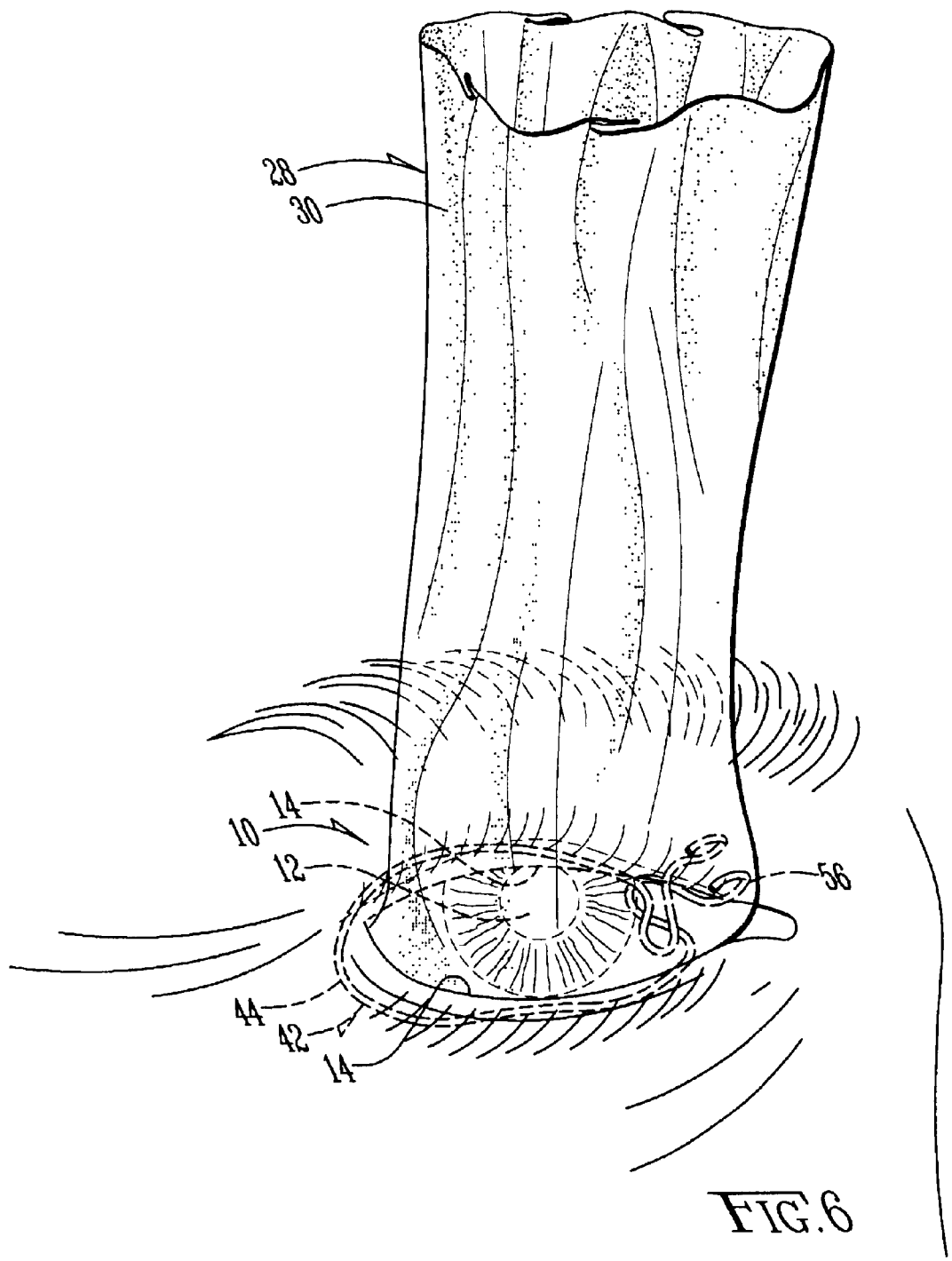
FIG. 6 is a perspective view of the preliminary steps of installing the speculum-drape of the invention.
Figure 7:
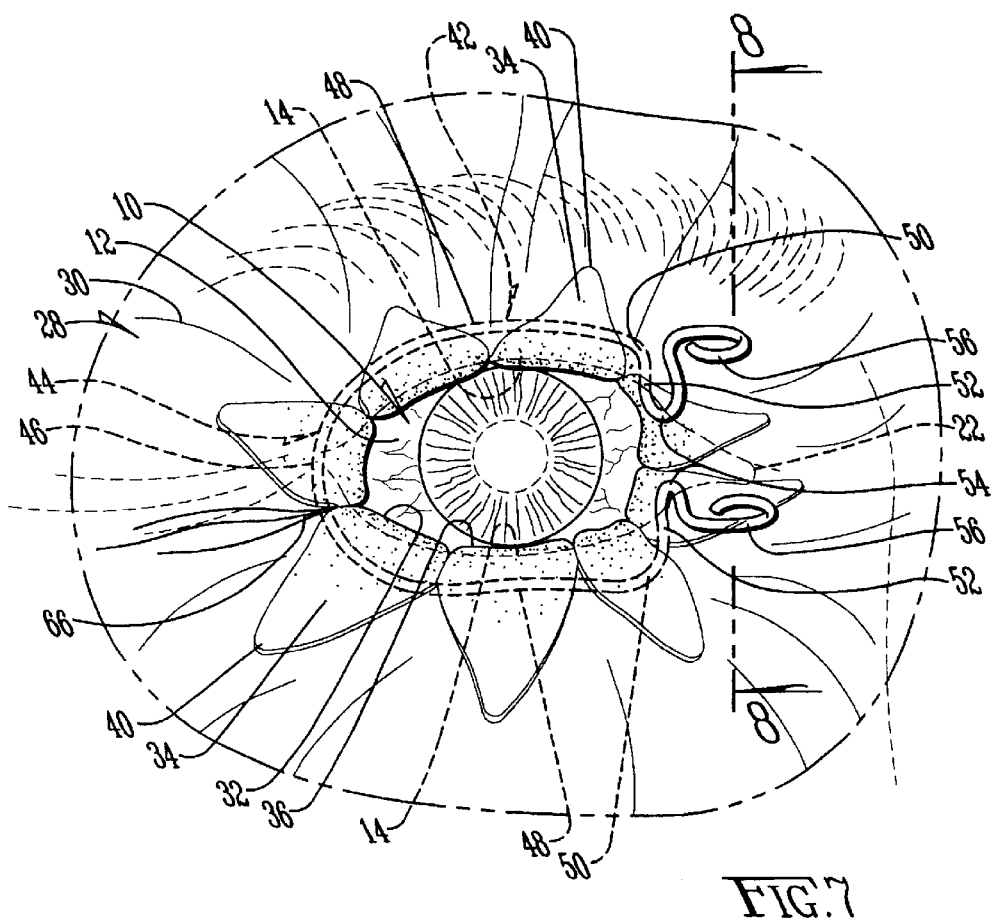
FIG. 7 is a perspective view of the invention after being installed on a surgical patient.
Figure 8:
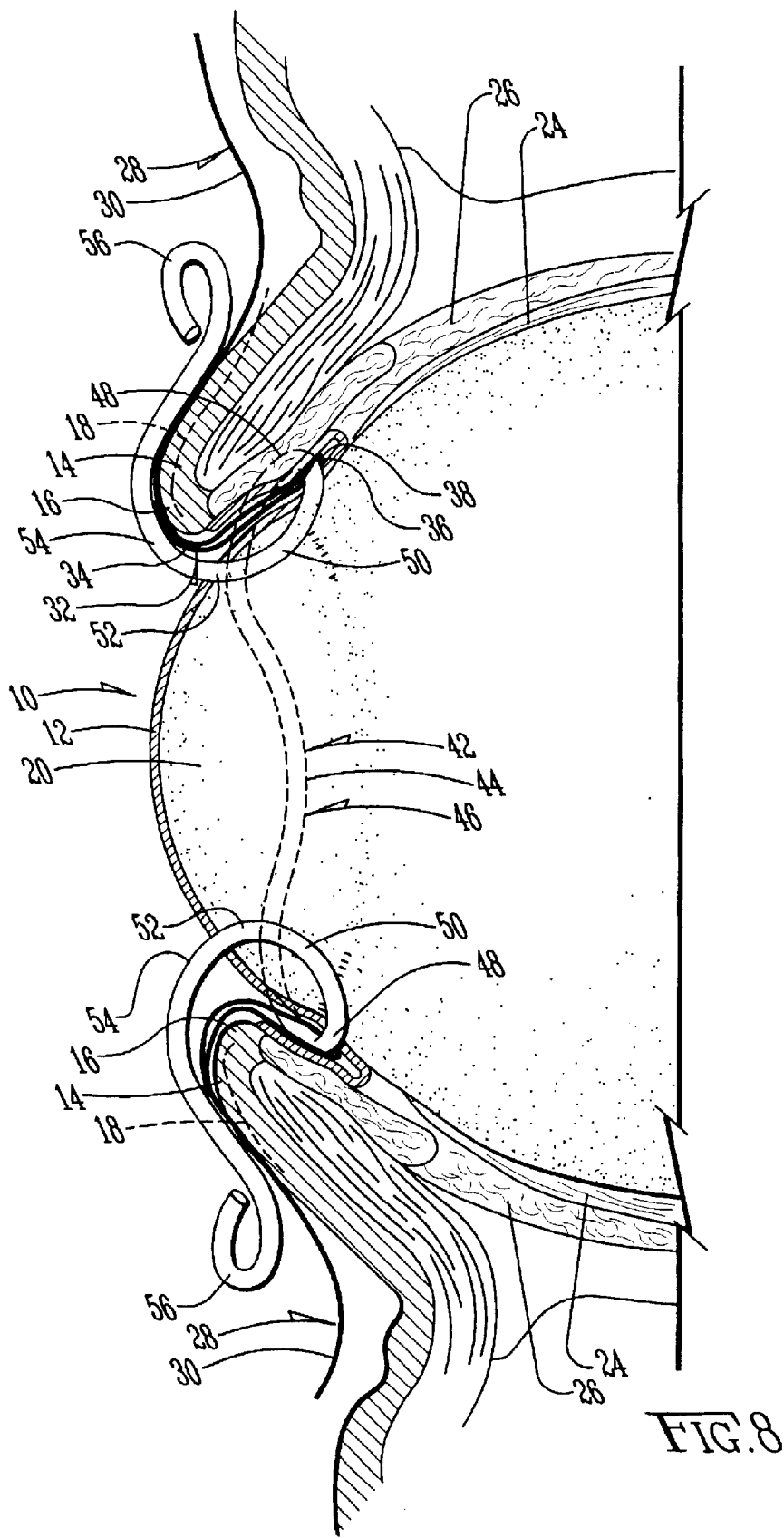
FIG. 8 is an enlarged scale sectional view taken on line 8—8 of FIG. 7.
Figure 12:
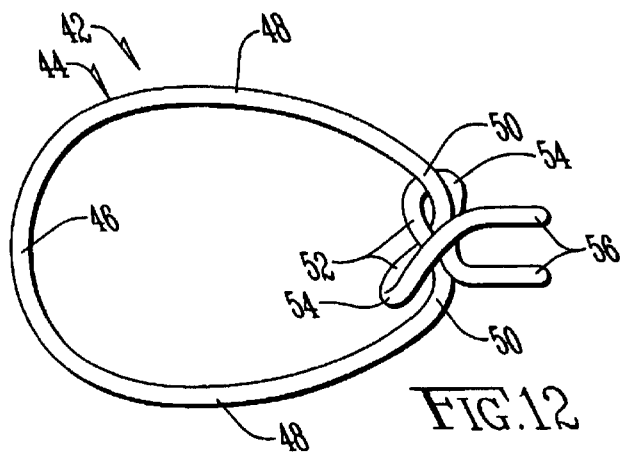
FIG. 12 is a plan view of FIG. 10.
Figure 18:
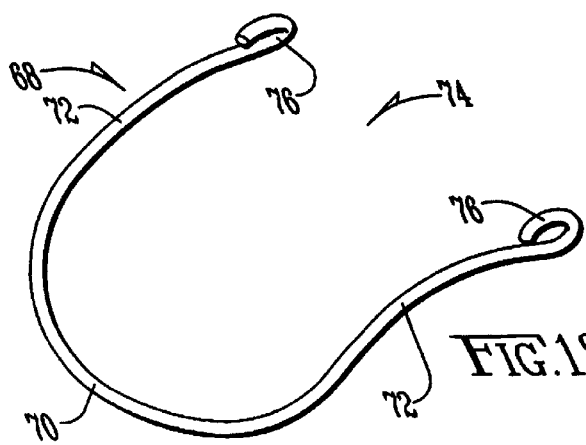
FIG. 18 is a perspective view of an alternate form of the speculum.
Figure 19:
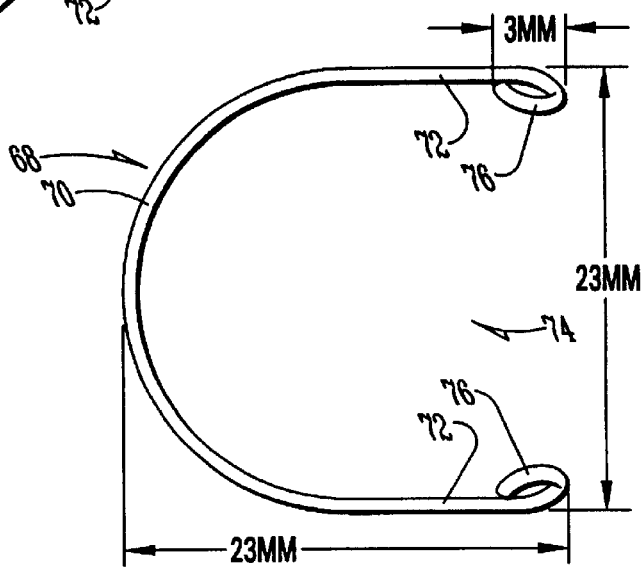
FIG. 19 is a plan view of FIG. 18.
Figure 20:
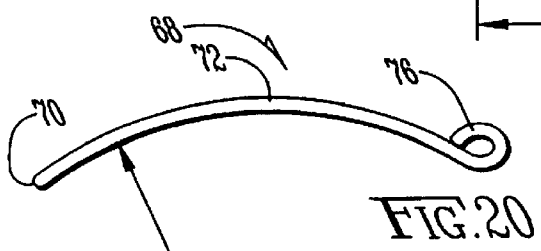
FIG. 20 is a side elevational view of FIG. 18 as viewed from the top.

With reference to FIGS. 6, 7 and 8, the human eye 10 includes globe 12, eyelids 14, lid margins 16, and eyelashes 18 (FIG. 18). The numeral 20 (FIG. 8) designates the cul-de-sac area around the eye 10 underneath the eyelids 14. The numeral 22 designates the nasal end of the eye (adjacent the nose), and the numeral 24 designates the lateral canthus tendon at the end of the eye opposite the nasal end 22. The palpebral aperture 26 is the open area of the eye between the eyelids 14.

Figure 2:
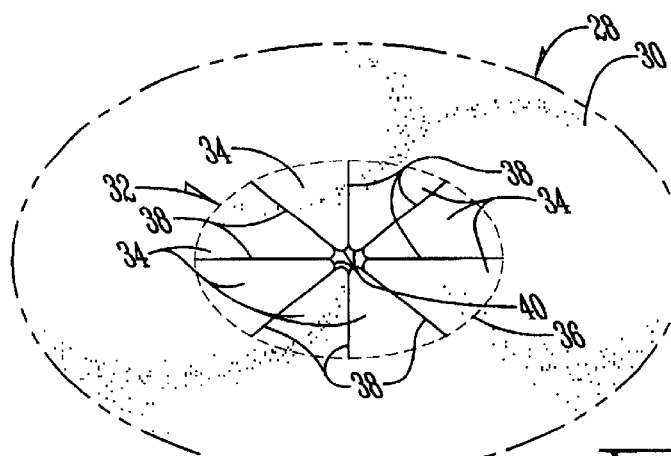
FIG. 2. is an enlarged scale view of the center of the drape material of FIG. 1.
Figure 3:
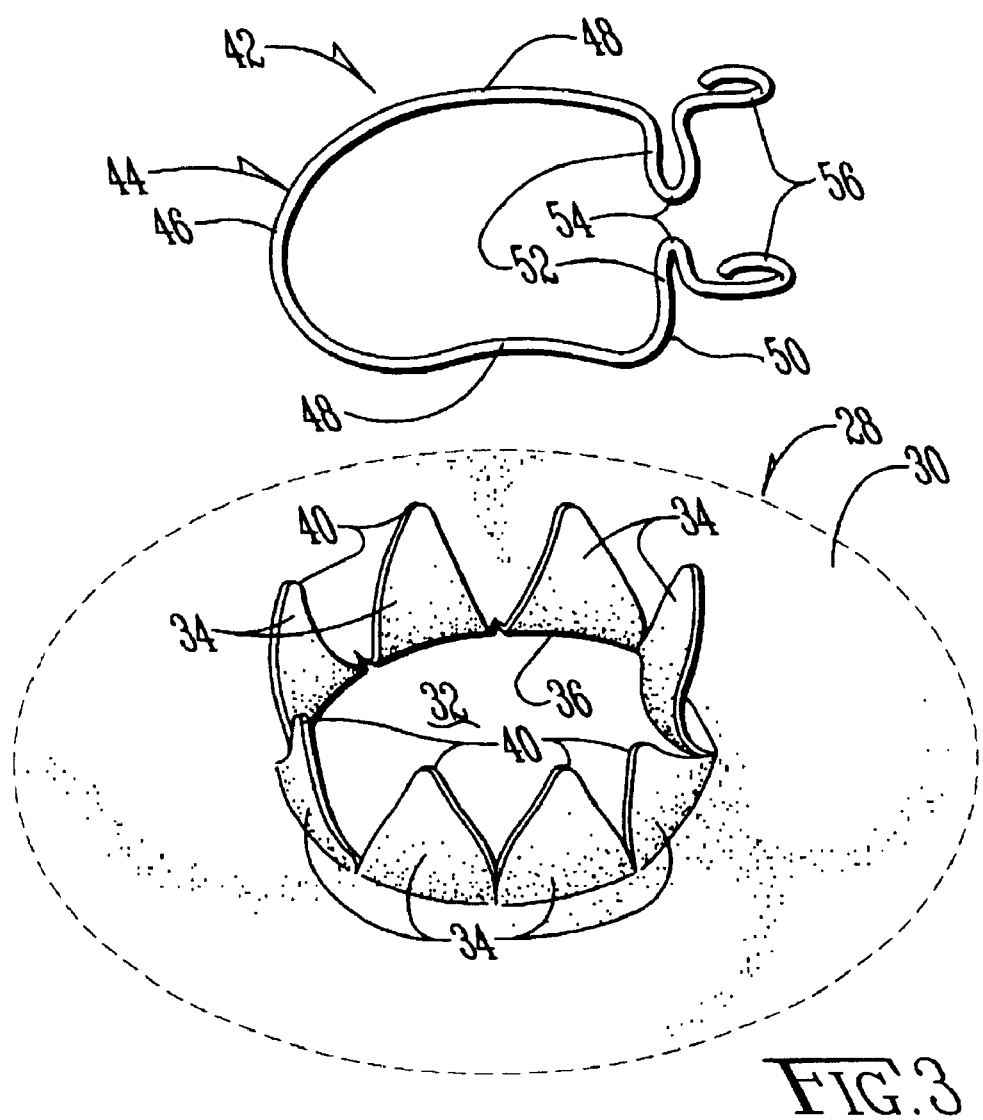
FIG. 3. is an enlarged scale exploded perspective view of the invention in a step that follows that of FIG. 1.
Figure 4:
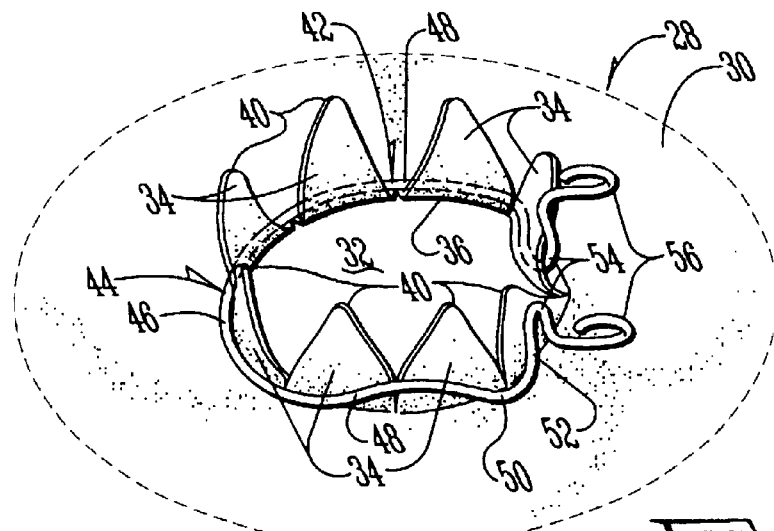
FIGS. 4 and 5 are views similar to FIG. 3 but in two subsequent stages of assembly.
Figure 5:
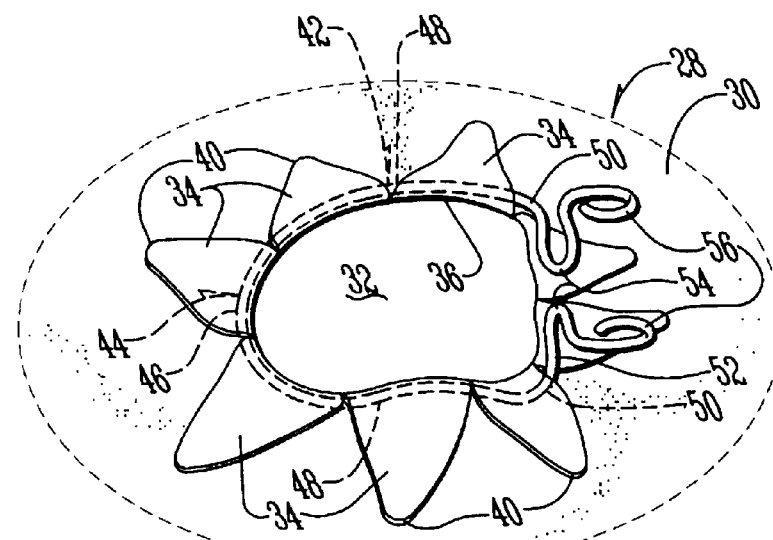

The speculum-drape 28 of FIG. 1 is comprised of a thin layer of drape material 30 having a center opening 32 formed as described below. The preferred drape material 30 is the fabric used in Steri-Drape 1035 made by the 3M Company. It is a microembossed polyethylene fabric approximately 40 microns (1.5 mils) thick. The circular opening 32 is formed creating flaps 34 by locating a circular fold line 36 (FIGS. 1 and 2), and cutting equally spaced diameters 38 across the fold line 36. The diameter of the opening 32 is approximately 25 mm. The inner tips 40 of the flaps 34 are cut into a rounded configuration to secure adhesion to the flaps to minimize the likelihood of the flaps catching on various objects during usage of the drape.

The speculum 42 is shown best in FIGS. 1 and 9–14. It is comprised preferably of a stainless steel wire 44 approximately 0.71 mm in diameter. Similarly, wire 44 could also be constructed of suitable plastic material. Wire 44 is bent into an arcuate or U-shaped configuration comprising an arcuate hoop 46 merging into opposing sides 48 which terminate respectively in shoulder loops 50. The shoulder loops 50 terminate in laterally extending arm 52 which each terminate in clip loops 54 which in turn terminate in upstanding spaced tabs 56. The configuration of speculum 42 in FIG. 11 shows the sides 48 in parallel relation when they are attached to drape material 30. Normally, the sides 48 extending diagonally outwardly from hoop 46 at an angle of about 95°, and are compressed into the position of FIG. 11 when attached to the drape material 30 as described hereafter.

Figure 13:
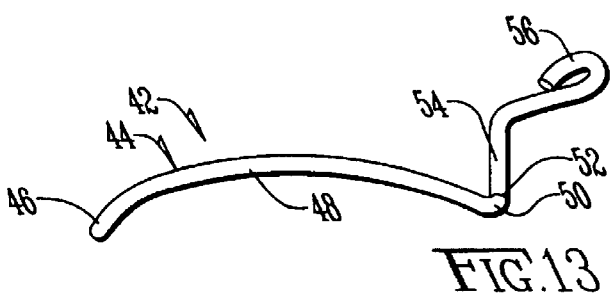
FIG. 13 is a side elevational view of the speculum as seen from the bottom of FIG. 12.
Figure 14:
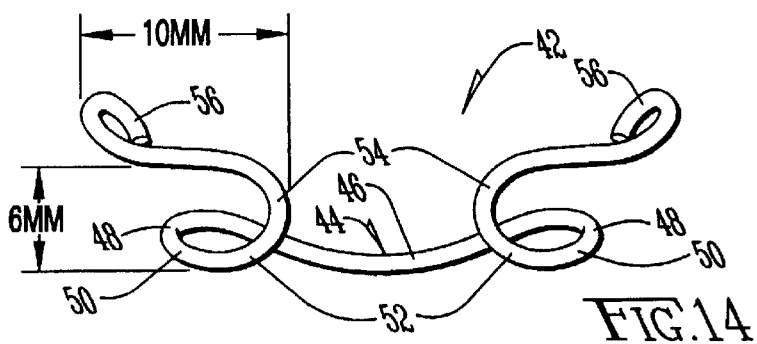
FIG. 14 is an end elevational view of the speculum as seen from the right hand end of FIG. 9.

With respect to FIG. 13, the wire 44 is arched so as to conform with contour of the cul-de-sac 20 of the eye.

With reference to FIGS. 1, 2 and 3, and 15, the speculum is slightly compressed as described above and dropped over the upstanding bent flaps 34 whereupon the flaps 34 are then bent downwardly over the wire 44 of the speculum 42, and are adhered to the outer or upper surface of the drape material 30 by any suitable means. Preferably, six of the flaps 30 will be bent over the hoop 46 and sides 44, which the remaining two flaps will extend through and over the inwardly extending arms 52 which connect the shoulder loop 50 and clip loop 54. When this is done, the speculum will be in the slightly compressed position of FIGS. 11 and 15.

Figure 15:
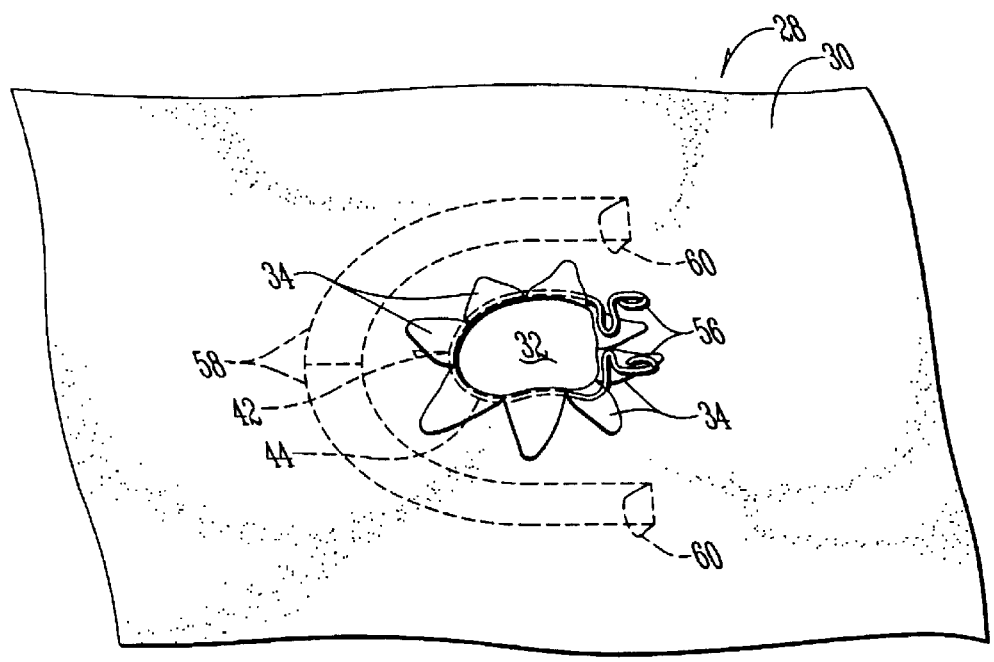
FIG. 15 is a perspective view of the assembled speculum-drape.
Figure 16:
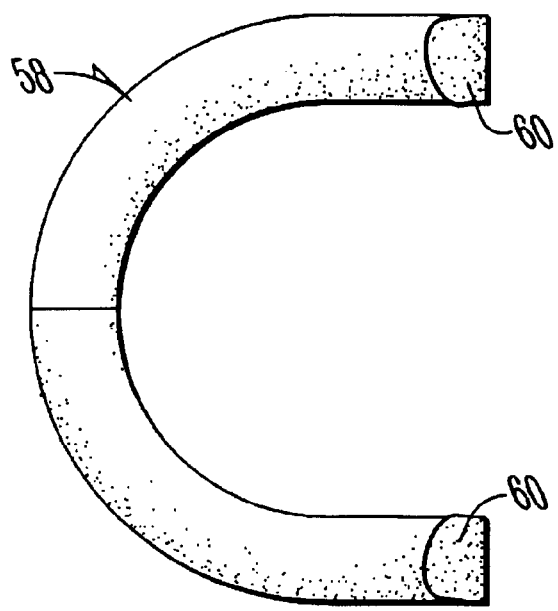
FIGS. 16 and 17 are plan views showing alternative adhesive strips.
Figure 17:
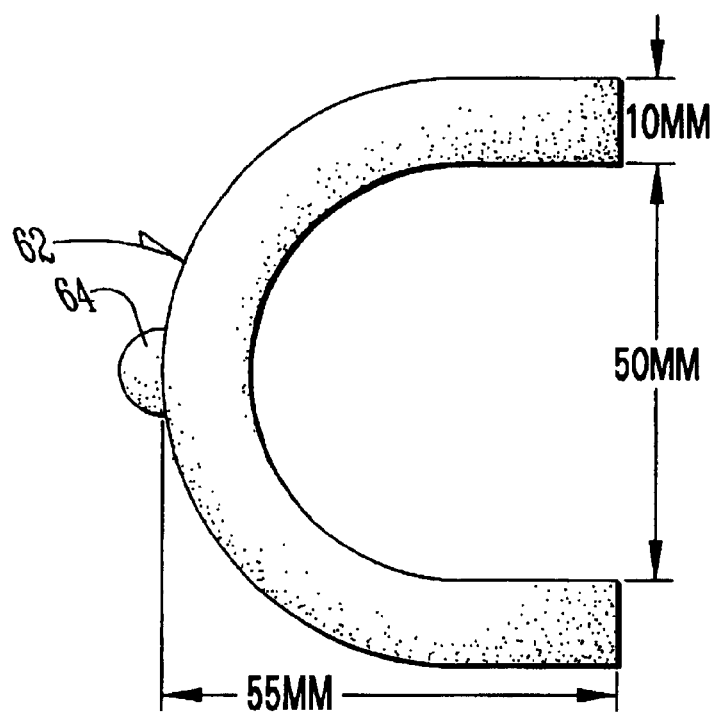

FIGS. 15 and 16 show a U-shaped adhesive strip 58 that has upstanding tabs 60 on the free ends thereof. These strips 58 are adhesively connected to the lower sides of the drape material 30 and have an adhesive outer surface for connection to the face of the patient. FIG. 17 shows an alternate adhesive strip 62 with a tab 64 for a similar purpose.

The stability of the speculum within the eye is maintained by the three-point suspension in the eye, namely, the location of the center of the hoop 46 under the tendon 24, and the arms 52 extending from shoulder loop 50.

In the placement of the drape, the fabric is gathered above the wire speculum (FIG. 6) and the surgeon compresses the open end of the speculum to reduce its dimensions. The lids are held open with the fingers of the opposite hand and the rounded end of the speculum is passed, with the drape attached, between the lids into the lateral (temporal) conjunctival sac. The clips engage the lid margins 16 near the internal (nasal) end of the lids and are released, allowing the spring action to open the palpebral aperture (the surface of the globe between the lid margins). These maneuvers will place the speculum beneath the lids with the drape fabric 30 exiting from the palpebral opening. As the fabric is smoothed and anchored to the skin surface with the adhesive strip, the eye will be further opened by the traction of the drape on the lid margin. With the drape in place, the lids and lashes are completely isolated from the surgical filed by the continuous barrier formed by the drape fabric. Traction on the drape fabric at the outer canthus tendon 24 by the adhesive strip 58 and the natural contour of the lid will produce a gutter effect. That gutter 66 (FIG. 7) will form a pathway for the exit of fluids from the surgical field by gravity.

More specifically, the assembled drape is positioned over the eye, and the drape material 30 is gathered together as shown in FIG. 6. the placement of the drape in the eye is as follows:

1. The drape, after folding (FIG. 6) is oriented so that the tabs 56 are towards the nasal end 22 and the hoop 46 is towards the lateral canthus tendon 24. The drape is held using the non-dominant hand from underneath with the tabs 56 on top.

2. The sides 48 of the speculum 48 are compressed slightly together with the thumb and forefinger of the non-dominant hand.

3. Then, with the dominant hand, the fabric is pulled into each of the speculum hooks while compressing the speculum with the finger and thumb of the other hand.

4. Then, while keeping the speculum compressed with the non-dominant hand, the other hand reaches over the speculum and the fabric is pulled over the hoop with the dominant hand and, with that hand, re-grasps the fabric 30 and the terminal tabs 56 beneath the fabric to keep them together. That maneuver gathers the drape fabric 30 at the shoulder loops 50 and transfers the drape to the dominant hand for insertion. Care should be taken so that the fabric has entered the base of the shoulder loops 50 leaving the shoulder loops exposed so that they can engage the lids 14 and allow the clip loops 54 to slide freely over the lid margin 16.

5. Then, the lids are held apart with the non-dominant hand (or an assistant's hand) and the hoop is placed beneath the lateral canthus tendon 24.

6. Next, the speculum 42 is lowered onto the eye so that the lids 14 move over the edge of the compressed speculum and drape. Then, the speculum tabs 56 is released.

7. Care should be taken to insure that the speculum is seated properly under the lids before smoothing the fabric 30 onto the surface of the lids. The fabric is folded over the lid margins and the speculum of the eyelids as best shown in FIGS. 7 and 8 so that the eyelids 14 and the eyelashes are completely covered.

8. For greater exposure, the drape may be anchored to the skin of the lids with adhesive tabs. Only enough traction is applied to expose the surgical filed of the globe 12, so that the speculum-drape 10 is not inadvertently displaced. Point traction on the temporal portion of the drape produces folds from the lateral canthus angle will provide a gutter 66 (FIG. 7) for drainage of the surgical filed. That traction can be created with an adhesive taps or a clamp. Most of the time, the weight of the drape fabric and/or surrounding towels or drapes will hold the drape in place without adhesive.

The location of the speculum-drape 28 after the above insertion process is best shown in FIG. 7.

After surgery, the speculum-drape 10 is removed essentially by reversing the above process whereby the speculum 28 is compressed by squeezing the tabs 56 together, and slidably withdrawing the drape-clad speculum in a direction towards the nasal end 22. The adhesive of the drape to the skin will be released as the drape is removed.

The form of a gutter or fluid overflow path as discussed in step 8 above provides for the beneficial exodus of fluid during surgery.

Figure 21:
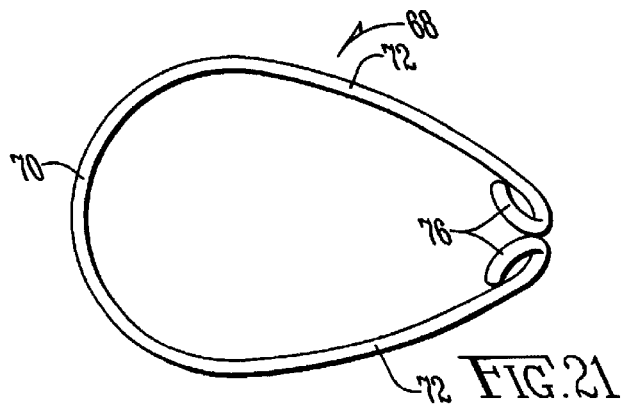
FIG. 21 is a plan view of the speculum of FIG. 19 in a compressed state.

An alternate U-shaped speculum 68 is shown in FIGS. 18–21. FIG. 18 shows the speculum 68 with a hoop portion 70 and generally parallel arched sides 72 (20 mm radius) extending from the hoop portion 70 towards open end 74. The ends of sides 72 adjacent open end 74 terminate in clips or tabs 76 which serve the same purpose as clips on tabs 56 previously described. FIG. 21 shows speculum 68 in its compressed condition to speculum 42 in FIG. 10.

The use of speculum 68 and the insertion and withdrawal thereof into and from the eye as associated with a drape fabric is essentially identical to that of speculum 42 previously described. The clips or tabs 76 are grasped by the operator to compress the speculum 68 to the position of FIG. 21.

This invention includes at least the following important features:

1. A truly integrated speculum and drape that performs the functions of each functions in one device and performs them optimally.

2. The integration of the drape and speculum provides benefits and consistency of results that cannot be achieved by either device alone or in combination as separate devices. The two elements work in harmony to achieve the objectives such as consistently covering the lids and lashes and elevating the lids off the eye to reduce pressure, and allowing drainage of the surgical field by the gutter effect.

3. A speculum that places the spring pressure behind the lid rather than external to the eye.

4. Three point fixation of the speculum wire for greater stability.

5. The coverage and isolation of the lid margin is achieved without adhesives and is therefore not dependent on the condition of the tissues such as a wet or greasy surface that would interfere with adhesion.

6. The invention requires no additional hardware such as external arms for placement or adjustment, and it automatically positions the drape fabric in the optimum location just by placement of the speculum-drape.

It is therefore seen that this invention will accomplish at least all of its stated objectives.

I claim:

1. An integrated speculum-drape for eye surgery, comprising, a flexible fabric sheet of drape material having a center portion, an opening in the center portion having a perimeter complimentary in shape to the globe of the human eye, a resilient elongated speculum being generally of an arcuate shape and having opposite side portions connected by an arcuate hoop portion, and with ends terminating in upstanding clip elements, the sides and the hoop portion of the speculum being connected to the perimeter of the opening in the center portion of the drape material with the upstanding clip elements protruding upwardly in spaced condition from the drape material, whereupon movement of the clips toward each other will reduce the area of the speculum and the opening in the center portion of the drape material to allow the speculum to be inserted underneath the eyelids of a patient, whereupon release of the clips will allow the speculum and the center opening of the drape material to be resiliently held underneath the eyelids, whereupon the drape material can be folded over upon itself in a direction away from the globe of the eye to drape the area surrounding the patient's eye.

2. The speculum of claim 1 wherein the speculum is a generally U-shaped stainless steel wire.

3. The speculum-drape of claim 1 wherein the upstanding clip elements being comprised of a shoulder loop portion being at the end of sides connected to ends of the loop portions, and an arm extending away from the shoulder loop and terminating in an upward extending clip loop.

4. The speculum-drape of claim 3 wherein the hoop and the side portions dwell in a plane of arcuate shape to be complimentary in shape to the cul-de-sac of an eye.

5. The speculum-drape of claim 3 wherein the clip loops are substantially at right angles with respect to the plane of the fabric sheet when the sheet is in a substantially horizontal plane.

6. The speculum-drape of claim 1 wherein the lateral width of the speculum-drape is approximately 25 mm.

7. The speculum-drape of claim 1 wherein the length of the speculum-drape is approximately 30 mm.

8. The speculum-drape of claim 1 wherein the lateral width of the speculum-drape is approximately 25 mm and the length of the speculum-drape is approximately 30 mm.

9. The speculum-drape of claim 1 wherein the speculum-drape includes an elongated wire and the diameter of the wire is approximately 0.71 mm and the wire is of stainless steel material.

10. The speculum-drape of claim 1 wherein the speculum has three primary supporting engagement points with the eye with a first point being at a substantial center of the hoop portion, and the other two points being underneath and adjacent the clip elements.

11. The speculum-drape of claim 1 wherein the drape material has an adhesive portion to secure the speculum-drape to the patient, and tension is placed on the drape material in a direction away from the eye before the drape material is secured to the patient so as to keep the eyelids in an open condition.

12. The speculum of claim 1 wherein the sides of the speculum are arched in shape.

13. A method of draping a patient's eye for a surgical procedure, comprising,
supplying a resilient elongated speculum being generally of an arcuate shape and having opposite side portions connected by an arcuate hoop portion, and with ends terminating in upstanding clip elements,
inserting into a patient's eye a drape having an opening complimentary in shape to the patient's eye, by compressing the speculum secured to a drape portion around the perimeter of the opening by applying pressure to the clip elements, and locating the speculum and the portion of the drape attached to the speculum into the cul-de-sac of the eye underneath the eyelids of the patient, and releasing the compression of the speculum so that the speculum with the drape attached will expand underneath the eyelids and be resiliently held in place against an underneath surface of the eyelid to hold the draped eyelid in a retracted position around the globe of the eye where surgery is to be conducted,
and allowing the remainder of the drape to cover the area of the patient's face around the eye.

14. The method of claim 13 wherein a portion of the drape around the eye is creased to create a fluid gutter for discharging fluid from the eye during surgery.

15. The method of claim 13 wherein the eyelids are manually held in an open position, and the arcuate hoop portion of the speculum is first slidably inserted into the cul-de-sac.

16. The method of claim 13 wherein the speculum is U-shaped with an arcuate end and an opposite open end.

17. An integrated speculum-drape for eye surgery, comprising,
a flexible fabric sheet of drape material having a center portion,
an opening in the center portion having a perimeter complimentary in shape to the globe of the human eye,
a resilient elongated speculum being generally of an arcuate shape and having opposite side portions connected by an arcuate hoop portion, and with ends terminating in clip elements,
the sides and the hoop portion of the speculum being connected to the perimeter of the opening in the center portion of the drape material with the clip elements protruding in spaced condition from the drape material, whereupon movement of the clips toward each other will reduce the area of the speculum and the opening in the center portion of the drape material to allow the speculum to be inserted underneath the eyelids of a patient, whereupon release of the clips will allow the speculum and the center opening of the drape material to be resiliently held underneath the eyelids, whereupon the drape material can be folded over upon itself in a direction away from the globe of the eye to drape the area surrounding the patient's eye.

18. The speculum of claim 17 wherein the speculum is a generally U-shaped.

19. The speculum-drape of claim 17 wherein the speculum-drape includes an elongated wire and the diameter of the wire is approximately 0.71 mm and the wire is of stainless steel material.

20. The speculum of claim 17 the sides of the speculum are arched in shape.

* * * * *